(12) United States Patent
Komura et al.

(10) Patent No.: US 10,829,474 B2
(45) Date of Patent: Nov. 10, 2020

(54) METHOD FOR PRODUCING HETEROCYCLIC COMPOUND

(71) Applicant: Takeda Pharmaceutical Company Limited, Chuo-ku, Osaka-shi, Osaka (JP)

(72) Inventors: Fumiya Komura, Osaka (JP); Yoshihiro Higuchi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 16/783,894

(22) Filed: Feb. 6, 2020

(65) Prior Publication Data

US 2020/0172509 A1    Jun. 4, 2020

Related U.S. Application Data

(62) Division of application No. 15/768,037, filed as application No. PCT/JP2016/080581 on Oct. 14, 2016, now Pat. No. 10,562,881.

(30) Foreign Application Priority Data

Oct. 16, 2015  (JP) ................. 2015-204164

(51) Int. Cl.
| | |
|---|---|
| *C07D 401/06* | (2006.01) |
| *C07D 401/14* | (2006.01) |
| *B01J 31/22* | (2006.01) |
| *C07B 61/00* | (2006.01) |

(52) U.S. Cl.
CPC ........ *C07D 401/06* (2013.01); *B01J 31/2208* (2013.01); *C07D 401/14* (2013.01); *B01J 2531/824* (2013.01); *C07B 61/00* (2013.01)

(58) Field of Classification Search
None
See application file for complete search history.

(56) References Cited

U.S. PATENT DOCUMENTS

| | | | |
|---|---|---|---|
| 5,312,975 | A | 5/1994 | Giordano et al. |
| 5,412,143 | A | 5/1995 | Giordano et al. |
| 9,598,398 | B2 | 3/2017 | Koike et al. |
| 2004/0248881 | A1 | 12/2004 | Carpino et al. |
| 2006/0189628 | A1 | 8/2006 | Rosse et al. |
| 2007/0213334 | A1 | 9/2007 | Carpino et al. |
| 2010/0234356 | A1 | 9/2010 | Rosse et al. |
| 2012/0171116 | A1 | 7/2012 | Tomczuk et al. |
| 2013/0090341 | A1 | 4/2013 | Koike et al. |
| 2014/0088118 | A1 | 3/2014 | Koike et al. |
| 2014/0088146 | A1 | 3/2014 | Koike et al. |
| 2014/0228373 | A1 | 8/2014 | Koike et al. |
| 2015/0376205 | A1 | 12/2015 | Koike et al. |
| 2016/0024049 | A1 | 1/2016 | Koike et al. |
| 2016/0039847 | A1 | 2/2016 | Tomczuk et al. |
| 2016/0326136 | A1 | 11/2016 | Koike et al. |
| 2017/0145031 | A1 | 5/2017 | Koike et al. |

FOREIGN PATENT DOCUMENTS

| | | |
|---|---|---|
| JP | H05-085986 A | 4/1993 |
| JP | 2006-527262 A | 11/2006 |
| JP | 2014-506253 A | 3/2014 |
| JP | 2014-528904 A | 10/2014 |
| WO | WO 2006/071958 A1 | 7/2006 |
| WO | WO 2013/054822 A1 | 4/2013 |
| WO | WO-2014/163161 A1 | 10/2014 |

OTHER PUBLICATIONS

Gould et al., "Salt selection for basic drugs," International Journal of Pharmaceutics, 1986, 33:201-217.
Stahl et al. "Electronic Supplementary Material for CrytEngComm", Jan. 1, 2005, retrieved from http://www.rsc.org/suppdata/ce/b5/b503309h/b503309h.doc, 1 page.
Stahl et al. "Handbook of Pharmaceutical salts, Table 1. Acids: Alphabetical Order", Handbook of Pharmaceutical Salts: Properties, Selection, and Use, Jan. 1, 2002, pp. 334-335.
Supplementary European Search Report for European Patent Appl. No. 16855540.7, dated Feb. 28, 2019, 4 pages.
Suzuki, Akira, "Suzuki-Miyaura Coupling (SMC) Hanno no Mondaiten," TCI Mail, 2009, 142:2-23.
Suzuki, Akira, "Suzuki-Miyaura Coupling (SMC) Hanno no Mondaiten," TCI Mail, 2009, 142:2-23, partial English translation of page 3.

*Primary Examiner* — Zinna Northington Davis
(74) *Attorney, Agent, or Firm* — Foley & Lardner LLP

(57) ABSTRACT

The present invention provides a production method of heterocyclic compound having an excellent CH24H inhibitory action, which is suitable for industrial production. In the present invention, a 2-halogenonicotinic acid or a reactive derivative thereof or a salt thereof is reacted with 4-benzyl-4-hydroxypiperidine acid addition salt to give a (4-benzyl-4-hydroxypiperidin-1-yl) (2-halogenopyridin-3-yl)methanone or a salt thereof, and then the obtained compound is reacted with pyridine-4-boronic acid or a reactive derivative thereof or a salt thereof in the presence of a metal catalyst and a base to give (4-benzyl-4-hydroxypiperidin-1-yl) (2,4'-bipyridin-3-yl)methanone or a salt thereof.

5 Claims, 4 Drawing Sheets

METHOD FOR PRODUCING HETEROCYCLIC COMPOUND

CROSS-REFERENCE TO RELATED APPLICATIONS

This application is a Divisional of U.S. application Ser. No. 15/768,037, which is the U.S. National Stage of PCT/JP2016/080581, filed Oct. 14, 2016, which claims priority to JP2015-204164, filed Oct. 16, 2015.

TECHNICAL FIELD

The present invention relates to a production method of a heterocyclic compound having a cholesterol 24-hydroxylase (in the present specification, sometimes to be abbreviated as "CH24H") inhibitory action.

BACKGROUND OF THE INVENTION

Patent Document 1 discloses a heterocyclic compound having an excellent CH24H inhibitory action, which is useful as an agent for the prophylaxis or treatment of neurodegenerative diseases (e.g., Alzheimer's disease, mild cognitive disorder, Huntington's disease, Parkinson's disease, amyotrophic lateral sclerosis, traumatic brain injury, cerebral infarction, glaucoma, multiple sclerosis and the like), epilepsy, schizophrenia and the like.

DOCUMENT LIST

Patent Document

Patent Document 1: WO 2013/054822

SUMMARY OF THE INVENTION

Problems to be Solved by the Invention

The present invention aims to provide a production method of a heterocyclic compound having an excellent CH24H inhibitory action, which is suitable for industrial production.

Means of Solving the Problems

The present inventors have conducted intensive studies in an attempt to solve the above-mentioned problem and found a production method suitable for industrial production, which resulted in the completion of the present invention. Accordingly, the present invention provides the following.

[1] A method of producing a (4-benzyl-4-hydroxypiperidin-1-yl) (2-halogenopyridin-3-yl)methanone or a salt thereof, which comprises reacting a 2-halogenonicotinic acid or a reactive derivative thereof or a salt thereof and a 4-benzyl-4-hydroxypiperidine acid addition salt.
[2] The method of the above-mentioned [1], wherein the 2-halogenonicotinic acid is 2-chloronicotinic acid.
[3] The method of any of the above-mentioned [1] to [2], wherein the reactive derivative is an acid chloride.
[4] The method of any of the above-mentioned [1] to [3], wherein the 4-benzyl-4-hydroxypiperidine acid addition salt is 4-benzyl-4-hydroxypiperidine benzoate.
[5] A method of producing (4-benzyl-4-hydroxypiperidin-1-yl) (2,4'-bipyridin-3-yl)methanone or a salt thereof, which comprises
step (1): a step of reacting a 2-halogenonicotinic acid or a reactive derivative thereof or a salt thereof and a 4-benzyl-4-hydroxypiperidine acid addition salt to give a (4-benzyl-4-hydroxypiperidin-1-yl) (2-halogenopyridin-3-yl)methanone or a salt thereof; and
step (2): a step of reacting the obtained (4-benzyl-4-hydroxypiperidin-1-yl) (2-halogenopyridin-3-yl)methanone or a salt thereof with pyridine-4-boronic acid or a reactive derivative thereof or a salt thereof in the presence of a metal catalyst and a base to give (4-benzyl-4-hydroxypiperidin-1-yl) (2,4'-bipyridin-3-yl)methanone or a salt thereof.
[6] The method of the above-mentioned [5], wherein the 2-halogenonicotinic acid is 2-chloronicotinic acid.
[7] The method of any of the above-mentioned [5] to [6], wherein the reactive derivative is an acid chloride.
[8] The method of any of the above-mentioned [5] to [7], wherein the 4-benzyl-4-hydroxypiperidine acid addition salt is 4-benzyl-4-hydroxypiperidine benzoate.
[9] The method of any of the above-mentioned [5] to [8], wherein the metal catalyst is bis(acetylacetonato)palladium (II).
[10] The method of any of the above-mentioned [5] to [9], wherein the base is sodium carbonate.

Effect of the Invention

Since the production method of the present invention is suitable for industrial production, it is a very useful method. According to the production method of the present invention, a heterocyclic compound having an excellent CH24H inhibitory action: (4-benzyl-4-hydroxypiperidin-1-yl) (2,4'-bipyridin-3-yl)methanone or a salt thereof, and a compound useful as an intermediate for producing the above-mentioned heterocyclic compound: a (4-benzyl-4-hydroxypiperidin-1-yl) (2-halogenopyridin-3-yl)methanone or a salt thereof can be produced with high purity and/or in high yield. In addition, according to the production method of the present invention, the above-mentioned compounds can be produced by easy procedure.

DETAILED DESCRIPTION OF THE INVENTION

Figure 1:
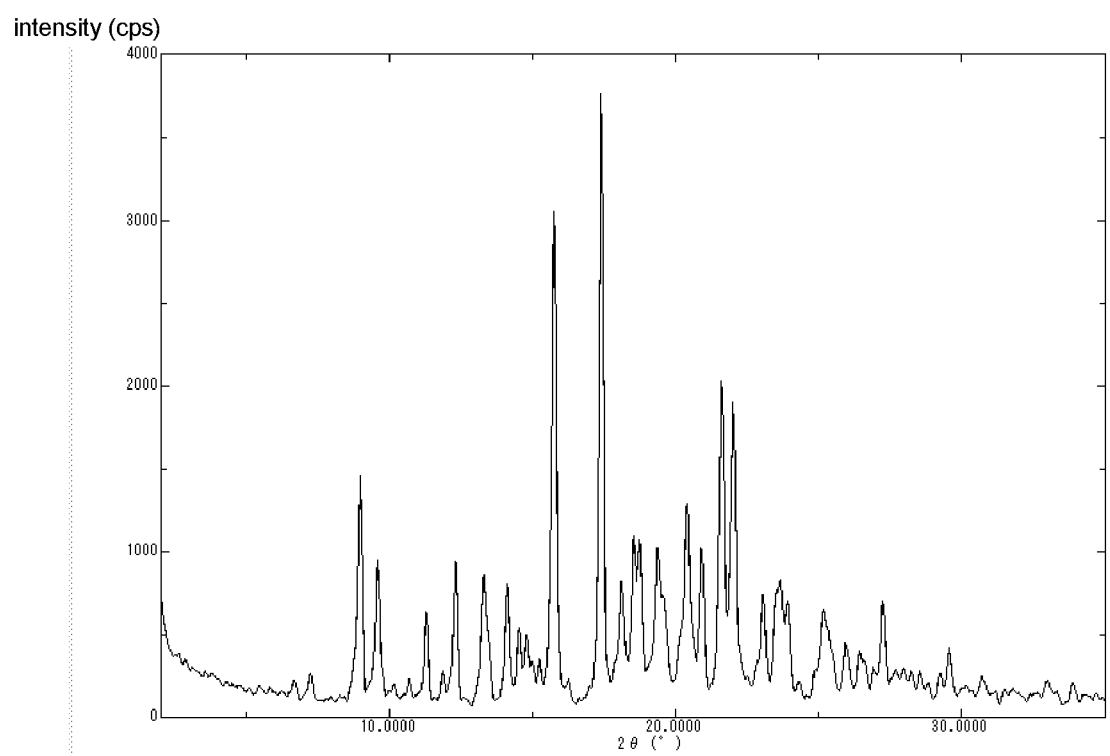
FIG. 1 shows the powder X-ray diffraction pattern of the milled product obtained in Reference Example 1.

The following each step can be performed without solvent, or by dissolving or suspending the raw material compound in a suitable solvent prior to the reaction. In this case, solvent may be used alone, or two or more kinds of these solvents may be mixed in an appropriate ratio and used. Specific examples of the solvent used in the production method of the present invention include the followings.
alcohols: methanol, ethanol, 1-propanol, 2-propanol, tert-butyl alcohol, 2-methoxyethanol etc.
ethers: diethyl ether, diisopropyl ether, diphenyl ether, tetrahydrofuran, 1,4-dioxane, 1,2-dimethoxyethane etc. aromatic hydrocarbons: benzene, chlorobenzene, toluene, xylene etc.

saturated hydrocarbons: cyclohexane, hexane etc.
amides: N,N-dimethylformamide (DMF), N,N-dimethylacetamide, hexamethylphosphoric triamide etc.
halogenated hydrocarbons: dichloromethane, chloroform, carbon tetrachloride, 1,2-dichloroethane etc.
nitriles: acetonitrile, propionitrile etc.
sulfoxides: dimethyl sulfoxide etc.
aromatic organic bases: pyridine, lutidine etc.
anhydrides: acetic anhydride etc.
organic acids: formic acid, acetic acid, propionic acid, trifluoroacetic acid, methanesulfonic acid etc.
inorganic acids: hydrochloric acid, sulfuric acid etc.
esters: methyl acetate, ethyl acetate, butyl acetate etc.
ketones: acetone, methyl ethyl ketone etc. water Specific examples of the base or acid scavenger used in the production method of the present invention include the followings.
inorganic bases: sodium hydroxide, potassium hydroxide, magnesium hydroxide etc.
basic salts: sodium carbonate, potassium carbonate, cesium carbonate, calcium carbonate, sodium hydrogencarbonate etc.
organic bases: triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, imidazole and the like
metal alkoxides: sodium methoxide, sodium ethoxide, potassium tert-butoxide etc.
alkali metal hydrides: sodium hydride, potassium hydride etc.
metal amides: sodium amide, lithium diisopropylamide, lithium hexamethyldisilazide etc.
organic lithium reagents: methyllithium, n-butyllithium, sec-butyllithium, tert-butyllithium etc.

Specific examples of the acid or acid catalyst used in the production method of the present invention include the followings.
inorganic acids: hydrochloric acid, sulfuric acid, nitric acid, hydrobromic acid, phosphoric acid etc.
organic acids: acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid etc.
Lewis acids: boron trifluoride ether complex, zinc iodide, anhydrous aluminium chloride, anhydrous zinc chloride, anhydrous iron chloride etc.

(4-Benzyl-4-hydroxypiperidin-1-yl)(2,4'-bipyridin-3-yl)methanone or a salt thereof can be produced according to the following steps (1) and (2).
Step (1)
A (4-benzyl-4-hydroxypiperidin-1-yl) (2-halogenopyridin-3-yl)methanone or a salt thereof can be produced by reacting a 2-halogenonicotinic acid or a reactive derivative thereof or a salt thereof and a 4-benzyl-4-hydroxypiperidine acid addition salt.

Examples of the acid addition salt in the 4-benzyl-4-hydroxypiperidine acid addition salt include salts with inorganic acid such as hydrochloric acid, hydrobromic acid, nitric acid, sulfuric acid, phosphoric acid and the like; and salts with organic acid such as formic acid, acetic acid, trifluoroacetic acid, phthalic acid, fumaric acid, oxalic acid, tartaric acid, maleic acid, citric acid, succinic acid, malic acid, benzoic acid, methanesulfonic acid, benzenesulfonic acid, p-toluenesulfonic acid and the like. Among them, preferred are salts with benzoic acid, oxalic acid and maleic acid, and particular preferred is a salt with benzoic acid. The (4-benzyl-4-hydroxypiperidin-1-yl) (2-halogenopyridin-3-yl)methanone or a salt thereof can be produced with high purity and/or in high yield, by use of a 4-benzyl-4-hydroxypiperidine acid addition salt, particularly a salt of the compound with benzoic acid.

Examples of the 2-halogenonicotinic acid include 2-chloronicotinic acid, 2-bromonicotinic acid, 2-iodonicotinic acid and the like. Among them, preferred is 2-chloronicotinic acid. Examples of the reactive acid derivative in the reactive derivative of the 2-halogenonicotinic acid include acid halides such as an acid chloride, an acid bromide and the like; acid amides with pyrazole, imidazole, benzotriazole and the like; mixed anhydrides with acetic acid, propionic acid, butyric acid and the like; acid azides; activated esters such as a diethoxyphosphorate ester, a diphenoxyphosphorate ester, a p-nitrophenyl ester, a 2,4-dinitrophenyl ester, a cyanomethyl ester, a pentachlorophenyl ester, an ester with N-hydroxysuccinimide, an ester with N-hydroxyphthalimide, an ester with 1-hydroxybenzotriazole, an ester with 6-chloro-1-hydroxybenzotriazole, an ester with 1-hydroxy-1H-2-pyridone, and the like; activated thioesters such as a 2-pyridyl thioester, a 2-benzothiazolyl thioester and the like, and the like. Among them, preferred are acid halides, and particularly preferred is an acid chloride. The 2-halogenonicotinic acid and a reactive derivative thereof may be in the form of a salt. Examples of such salt include salts with inorganic acid such as hydrochloric acid, hydrobromic acid, nitric acid, sulfuric acid, phosphoric acid and the like; and salts with organic acid such as formic acid, acetic acid, trifluoroacetic acid, phthalic acid, fumaric acid, oxalic acid, tartaric acid, maleic acid, citric acid, succinic acid, malic acid, benzoic acid, methanesulfonic acid, benzenesulfonic acid, p-toluenesulfonic acid and the like. Among them, preferred is a hydrochloride. In this case, the salts are used together with inorganic bases, basic salts, organic bases and the like.

The 2-halogenonicotinic acid or a reactive derivative thereof or a salt thereof is preferably a reactive derivative of a 2-halogenonicotinic acid, more preferably an acid halide of 2-chloronicotinic acid, particularly preferably an acid chloride of 2-chloronicotinic acid.

The 2-halogenonicotinic acid or a reactive derivative thereof or a salt thereof is generally used in an amount of about 0.8 to 5 mol, preferably about 1.05 to 1.16 mol, per 1 mol of the 4-benzyl-4-hydroxypiperidine acid addition salt.

When a 2-halogenonicotinic acid or a salt thereof is used, the (4-benzyl-4-hydroxypiperidin-1-yl) (2-halogenopyridin-3-yl)methanone or a salt thereof may also be produced by reaction in the presence of a suitable condensing agent.

Examples of the condensing agent include N,N'-di-substituted carbodiimides such as N,N'-dicyclohexylcarbodiimide, 1-ethyl-3-(3-dimethylaminopropyl)carbodiimide (WSC) hydrochloride and the like; azolides such as N,N'-carbonyldiimidazole and the like; dehydrating agents such as N-ethoxycarbonyl-2-ethoxy-1,2-dihydroquinoline, phosphorus oxychloride, alkoxyacetylene and the like; 2-halogenopyridinium salts such as 2-chloromethylpyridinium iodide, 2-fluoro-1-methylpyridinium iodide and the like; phosphorylcyanides such as diethylphosphorylcyanide and the like; 2-(7-azabenzotriazol-1-yl)-1,1,3,3-tetramethyluronium hexafluorophosphate (HATU), O-(7-azabenzotriazol-1-yl)-N,N,N',N'-tetramethyluronium tetrafluoroborate (TATU) and the like.

This reaction is preferably carried out in a stream of an inert gas such as argon gas, nitrogen gas and the like.

This reaction is advantageously carried out in a solvent inert to the reaction. While the solvent is not particularly limited as long as the reaction proceeds, examples thereof include ethers, aromatic hydrocarbons, saturated hydrocarbons, amides, halogenated hydrocarbons, nitriles, sulfoxides, aromatic organic bases, and mixed solvents thereof and the like. Among them, preferred are aromatic hydrocarbons, amides and mixed solvents thereof, and particularly preferred is a mixed solvent of toluene and DMF.

The reaction may be carried out in the presence of an inorganic base, a basic salt, an organic base or the like in order to promote the reaction. In addition, when an acidic substance is released in the reaction system, an inorganic base, a basic salt, an organic base or the like may be used in order to remove acidic substance from the reaction system.

Especially, when 4-benzyl-4-hydroxypiperidine benzoate is used as a 4-benzyl-4-hydroxypiperidine acid addition salt, an inorganic base, particularly sodium hydroxide is preferably used in order to remove benzoic acid generated in the reaction system. The sodium hydroxide is generally used in an amount of about 1 to 10 mol, preferably about 2 to 5 mol, per 1 mol of the 4-benzyl-4-hydroxypiperidine benzoate.

While the reaction time varies depending on the reagent or solvent to be used, it is generally 10 min to 72 hr. The reaction temperature is preferably 0 to 100° C.

The thus-obtained (4-benzyl-4-hydroxypiperidin-1-yl) (2-halogenopyridin-3-yl)methanone or a salt thereof can be used directly as the reaction mixture or used as a crude product in the next reaction. It can also be isolated from the reaction mixture by a conventional method, and can be easily purified by a separation means such as recrystallization, distillation, chromatography and the like.

When a 2-halogenonicotinic acid or a reactive derivative thereof or a salt thereof, and a 4-benzyl-4-hydroxypiperidine acid addition salt are commercially available, the commercially available products can be directly used, or can be produced according to a method known per se.

Step (2)

(4-Benzyl-4-hydroxypiperidin-1-yl)(2,4'-bipyridin-3-yl) methanone or a salt thereof can be produced by reacting the (4-benzyl-4-hydroxypiperidin-1-yl) (2-halogenopyridin-3-yl)methanone or a salt thereof with pyridine-4-boronic acid or a reactive derivative thereof or a salt thereof in the presence of a metal catalyst and a base.

Examples of the reactive derivative or salt thereof of the pyridine-4-boronic acid include a pinacol ester [i.e., 4-(4,4,5,5-tetramethyl-1,3,2-dioxaborolan-2-yl)pyridine], a trimethyleneglycol ester [i.e., 4-(1,3,2-dioxaborinan-2-yl)pyridine], 4-pyridinetrifluoroborate or a salt thereof (e.g., a sodium salt, a potassium salt) and (4-pyridine)cyclic triolborate or a salt thereof (e.g., a sodium salt, a potassium salt). Among them, particularly preferred is pyridine-4-boronic acid.

The pyridine-4-boronic acid or a reactive derivative thereof or a salt thereof is generally used in an amount of about 0.8 to 10 mol, preferably about 1.18 to 1.31 mol, per 1 mol of the (4-benzyl-4-hydroxypiperidin-1-yl) (2-halogenopyridin-3-yl)methanone or a salt thereof.

Examples of the metal catalyst include palladium compounds [e.g.: palladium(II) acetate, bis(acetylacetonato)palladium(II), tetrakis(triphenylphosphine)palladium(0), dichlorobis(triphenylphosphine)palladium(II), dichlorobis (triethylphosphine)palladium(II), tris(dibenzylideneacetone)dipalladium(0), a complex of palladium(II) acetate and 1,1'-bis(diphenylphosphino)ferrocene, and the like]. Among them, preferred is bis(acetylacetonato)palladium (II). The metal catalyst is generally used in an amount of about 0.000001 to 1.0 mol, preferably about 0.005 to 0.030 mol, per 1 mol of the (4-benzyl-4-hydroxypiperidin-1-yl) (2-halogenopyridin-3-yl)methanone or a salt thereof. The metal catalyst is preferably used together with a phosphine ligand. Examples of the phosphine ligand include triphenylphosphine, tris(4-methoxyphenyl)phosphine, 4,5-bis(diphenylphosphino)-9,9-dimethylxanthene, tri-tert-butylphosphine and the like. In addition, a salt such as tri-tert-butylphosphine tetrafluoroborate may be used. The phosphine ligand is preferably tris(4-methoxyphenyl)phosphine. The combination of the metal catalyst and the phosphine ligand is preferably a combination of bis(acetylacetonato)palladium(II) and tris(4-methoxyphenyl)phosphine. The phosphine ligand is generally used in an amount of about 0.001 to 5 mol, preferably about 0.005 to 0.030 mol, per 1 mol of the (4-benzyl-4-hydroxypiperidin-1-yl) (2-halogenopyridin-3-yl)methanone or a salt thereof.

Examples of the base include inorganic bases, basic salts and the like. Among them, preferred are basic salts, and particularly preferred is sodium carbonate. When desired, the reaction may be carried out by adding an additive such as copper(I) cyanide, copper(I) bromide and the like. The base is generally used in an amount of about 1 to 20 mol, preferably about 2.8 to 3.2 mol, per 1 mol of the (4-benzyl-4-hydroxypiperidin-1-yl) (2-halogenopyridin-3-yl)methanone or a salt thereof. The additive is generally used in an amount of about 0.000001 to 5.0 mol, per 1 mol of the (4-benzyl-4-hydroxypiperidin-1-yl) (2-halogenopyridin-3-yl)methanone or a salt thereof.

When a metal catalyst unstable to oxygen is used in this reaction, the reaction is preferably carried out in a stream of an inert gas such as argon gas, nitrogen gas and the like.

This reaction is advantageously carried out in a solvent inert to the reaction. While the solvent is not particularly limited as long as the reaction proceeds, examples thereof include alcohols, ethers, aromatic hydrocarbons, saturated hydrocarbons, amides, halogenated hydrocarbons, nitriles, esters, water, mixed solvents thereof and the like. Among them, preferred are alcohols, water and mixed solvents thereof, and particularly preferred is a mixed solvent of tert-butanol and water.

While the reaction time varies depending on the reagent or solvent to be used, it is generally 1 min to 200 hr. The reaction temperature is preferably 0 to 150° C. The reaction may be carried out under microwave irradiation in order to promote the reaction.

When pyridine-4-boronic acid or a reactive derivative thereof or a salt thereof is commercially available, the commercially available product can be directly used, or can be produced according to a method known per se.

The thus-obtained (4-benzyl-4-hydroxypiperidin-1-yl) (2,4'-bipyridin-3-yl)methanone or a salt thereof can be isolated and purified from the reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

For example, the (4-benzyl-4-hydroxypiperidin-1-yl) (2,4'-bipyridin-3-yl)methanone can be crystallized from ethyl acetate/acetone/n-heptane or ethanol/n-heptane. Among them, crystallization from ethanol/n-heptane is preferable.

The (4-benzyl-4-hydroxypiperidin-1-yl) (2,4'-bipyridin-3-yl)methanone and (4-benzyl-4-hydroxypiperidin-1-yl) (2-halogenopyridin-3-yl)methanone may be in the form of a salt. While the salt is not particularly limited as long as the reaction is achieved, examples thereof include salts with inorganic acid, salts with organic acid, salts with acidic amino acid, and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, benzoic acid, methanesulfonic acid, benzenesulfonic acid, p-toluenesulfonic acid and the like. Preferable examples of the salt with acidic amino acid include salts with aspartic acid, glutamic acid and the like. The salt can be produced by addition of inorganic acid, organic acid or acidic amino acid, according to a method known per se.

EXAMPLES

The present invention is explained in detail by referring to the following Example, which are not to be construed as limitative, and the invention may be changed within the scope of the present invention.

In the following Example and Reference Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bonded silica gel. In HPLC (high performance liquid chromatography), C18 means use of octadecyl-bonded silica gel. The ratios of elution solvents are volume mixing ratios, unless otherwise specified.

In the following Example and Reference Examples, the following abbreviations are used.
THF: tetrahydrofuran
DMF: N,N-dimethylformamide
[M+H]$^+$: molecular ion peak
M: mol concentration
DSC: differential scanning calorimetry
TGA: thermogravimetric analysis $^1$H NMR (proton nuclear magnetic resonance spectrum) was measured by Fourier-transform type NMR. For the analysis, ACD/Spectrusprocessor (trade name) and the like were used. Peaks with very mild protons such as a hydroxy group, an amino group and the like are not described.

MS (mass spectrum) was measured by LC/MS (liquid chromatography mass spectrometer). As ionization method, ESI (Electro Spray Ionization) method was used. The data indicates actual measured value (found). Generally, molecular ion peaks are observed. For example, in the case of a compound having a tert-butoxycarbonyl group (-Boc), a peak after elimination of a tert-butoxycarbonyl group or a tert-butyl group may be observed as a fragment ion. In the case of a compound having a hydroxy group (—OH), a peak after elimination of H$_2$O may be observed as a fragment ion. In the case of a salt, a molecular ion peak or fragment ion peak of free form is generally observed.

EXAMPLE (4-benzyl-4-hydroxypiperidin-1-yl) (2,4'-bipyridin-3-yl)methanone

A) (4-benzyl-4-hydroxypiperidin-1-yl) (2-chloropyridin-3-yl)methanone

To a mixture of 2-chloronicotinic acid (53.7 kg), toluene (252 kg) and DMF (0.55 kg) was added thionyl chloride (47.9 kg), and the mixture was stirred under nitrogen atmosphere at 90° C. for 1 hr. The reaction mixture was concentrated under reduced pressure, the residue was dissolved in THF (216 kg), and 2M aqueous sodium hydroxide solution (419 kg) and 4-benzyl-4-hydroxypiperidine benzoate (97.0 kg) were added thereto. The reaction mixture was stirred under nitrogen atmosphere at room temperature for 1 hr, 10% aqueous potassium carbonate solution (291 kg) was added thereto, and the mixture was extracted with ethyl acetate (524 kg). The extract was concentrated under reduced pressure, and ethanol (46 kg) and n-heptane (365 kg) were added thereto to give the title compound (96.8 kg) as crystals.

MS (ESI+): [M+H]$^+$331.1.

B) (4-benzyl-4-hydroxypiperidin-1-yl) (2,4'-bipyridin-3-yl)methanone

A mixture of (4-benzyl-4-hydroxypiperidin-1-yl) (2-chloropyridin-3-yl)methanone (60.0 kg), bis(acetylacetonato)palladium(II) (0.28 kg), tris(4-methoxyphenyl)phosphine (0.32 kg), pyridine-4-boronic acid (27.9 kg), sodium carbonate (57.6 kg), tert-butanol (482 kg) and water (300 kg) was stirred overnight under nitrogen atmosphere at 85° C. To the reaction mixture was added 20% aqueous sodium hydrogensulfite solution (600 kg), and the mixture was extracted with ethyl acetate (271 kg). The extract was washed with 1M hydrochloric acid (611 kg), 20% aqueous potassium carbonate solution (480 kg) and 10% aqueous potassium carbonate solution (300 kg), and the solvent was evaporated under reduced pressure. To the residue were added acetone (143 kg) and n-heptane (206 kg) to give the crystals (58.1 kg) of the title compound.

$^1$H NMR (300 MHz, CDCl$_3$) δ 0.05-1.73 (5H, m), 2.34-2.53 (1H, m), 2.61-3.25 (4H, m), 4.37-4.64 (1H, m), 6.96-7.16 (2H, m), 7.19-7.34 (3H, m), 7.42 (1H, dd, J=7.6, 4.9 Hz), 7.54-7.85 (3H, m), 8.60-8.83 (3H, m).

Reference Example 1

(4-Benzyl-4-hydroxypiperidin-1-yl) (2,4'-bipyridin-3-yl)methanone was produced by the following method different from the production method of the present invention.

A) Tert-Butyl 2-Chloronicotinate

To a mixture of 2-chloronicotinic acid (10.0 kg), toluene (43.4 kg) and 1,2-dimethoxyethane (43.4 kg) was added thionyl chloride (9.1 kg), and the mixture was stirred under nitrogen atmosphere at 80° C. for 3 hr. The reaction mixture was concentrated under reduced pressure, the residue was dissolved in THF (88.9 kg), and potassium tert-butoxide (8.4 kg) and THF (88.9 kg) were added thereto at −5° C. To the reaction mixture was added aqueous sodium chloride solution, and the mixture was extracted with toluene. The extract was concentrated under reduced pressure, and 1,2-dimethoxyethane was added thereto to give the title compound (13.1 kg).

B) Tert-Butyl (2,4'-bipyridine)-3-carboxylate

To a mixture of sodium carbonate (13.8 kg), 1,2-dimethoxyethane (80.7 kg) and water (93.0 kg) were added pyridine-4-boronic acid (6.4 kg), tert-butyl 2-chloronicotinate (9.3 kg) and tetrakistriphenylphosphine palladium (1.5 kg), and the mixture was stirred under nitrogen atmosphere at 80° C. for 24 hr. To the reaction mixture was added ethyl acetate, and the mixture was concentrated under reduced pressure. Sodium chloride was added thereto, and the mixture was extracted with ethyl acetate. The extract was concentrated under reduced pressure to give the title compound (10.6 kg).

C) (2,4'-bipyridine)-3-carboxylic Acid Dihydrochloride

To a mixture of tert-butyl (2,4'-bipyridine)-3-carboxylate (10.6 kg) and ethyl acetate (57.4 kg) were added 6M hydrochloric acid and 4N hydrochloric acid/ethyl acetate solution, and the mixture was stirred under nitrogen atmosphere at 25° C. for 22 hr to give the crystals (11.1 kg) of the title compound.

D) (2,4'-bipyridine)-3-carboxylic Acid Hydrochloride (Purification Step)

To a mixture of methanol (79.2 kg) and water (11.0 kg) was added (2,4'-bipyridine)-3-carboxylic acid dihydrochloride (11.1 kg), and the compound was dissolved under nitrogen atmosphere at 65° C. The solution was cooled to room temperature, and ethyl acetate was added thereto to give the crystals (7.9 kg) of the title compound.

E) (4-benzyl-4-hydroxypiperidin-1-yl) (2,4'-bipyridin-3-yl)methanone

To THF (51.6 kg) were added (2,4'-bipyridine)-3-carboxylic acid hydrochloride (7.5 kg), diisopropylethylamine (6.1 kg), 4-benzyl-4-hydroxypiperidine (6.7 kg), 1-hydroxybenzotriazole (0.5 kg) and 1-ethyl-3-(3-dimethylaminopropyl)carbodiimide hydrochloride (7.3 kg), and the mixture was stirred under nitrogen atmosphere at 25° C. for 3 hr. To the reaction mixture was added aqueous potassium carbonate solution, and the mixture was extracted with ethyl acetate. The extract was concentrated under reduced pressure, and n-heptane was added thereto to give the title compound (10.5 kg).

F) (4-benzyl-4-hydroxypiperidin-1-yl) (2,4'-bipyridin-3-yl)methanone (Purification Step)

To isopropyl alcohol (39.1 kg) was added (4-benzyl-4-hydroxypiperidin-1-yl) (2,4'-bipyridin-3-yl)methanone (10.0 kg), and the compound was dissolved under nitrogen atmosphere at 70° C. The solution was concentrated under reduced pressure, and water was added thereto to give the crystals (8.3 kg) of the title compound.

The obtained crystals were pulverized using jet mill, and the melting point of the milled product was measured under the following conditions.

The melting point here means onset melting temperature in the measurement result.
measurement apparatus: METTLER TOLEDO (TGA/DSC1&DSC1)
measurement conditions:
 temperature rise rate: 5° C./min
 atmosphere: $N_2$
measurement result: 149° C.

Reference Example 2

Production of 4-benzyl-4-hydroxypiperidine Benzoate

To a mixture of magnesium (17.6 kg), iodine (9.7 kg) and THF (605 kg) were added benzyl chloride (70.2 kg) and THF (189 kg), and the mixture was stirred under nitrogen atmosphere at 25° C. for 2 hr. To the reaction mixture were added tert-butyl 4-oxopiperidine-1-carboxylate (85 kg) and THF (151 kg), and the mixture was stirred at 25° C. for 1 hr. To the reaction mixture was added aqueous ammonium chloride solution, and the organic layer was extracted. The extract was washed with 6M hydrochloric acid and 8M aqueous sodium hydroxide solution, and the solvent was evaporated under reduced pressure. To the residue were added benzoic acid and isopropyl alcohol to give the title compound (97.8 kg).
elemental analysis value:
Calculated: C: 72.82, H: 7.40, N: 4.47
Found: C: 72.79, H: 7.34, N: 4.47

Reference Example 3

A) Preparation of Seed Crystals

To n-heptane (109 kg) and ethyl acetate (216 kg) were added (4-benzyl-4-hydroxypiperidin-1-yl) (2,4'-bipyridin-3-yl)methanone (66.4 kg) (obtained in the same manner as in Example) and ethanol (52.4 kg), and the compound was dissolved under nitrogen atmosphere at 70° C. The solution was cooled to room temperature, and n-heptane was added thereto to give crystals (58.1 kg) of (4-benzyl-4-hydroxypiperidin-1-yl) (2,4'-bipyridin-3-yl)methanone. The obtained crystals were pulverized using jet mill to give the seed crystals.

B) Purification of (4-benzyl-4-hydroxypiperidin-1-yl) (2,4'-bipyridin-3-yl)methanone To ethanol (118.4 g) was added (4-benzyl-4-hydroxypiperidin-1-yl) (2,4'-bipyridin-3-yl)methanone (60.0 g) obtained in Example, and the compound was dissolved at 70° C. To the solution was added n-heptane (41.0 g), and then the seed crystals (120 mg) obtained in Step A) and n-heptane (451.4 g) were added thereto to give the crystals (57.2 g) of the title compound. The melting point of the obtained crystals was measured under the conditions described in Reference Example 1. melting point: 164° C.

Reference Example 4

Figure 4:
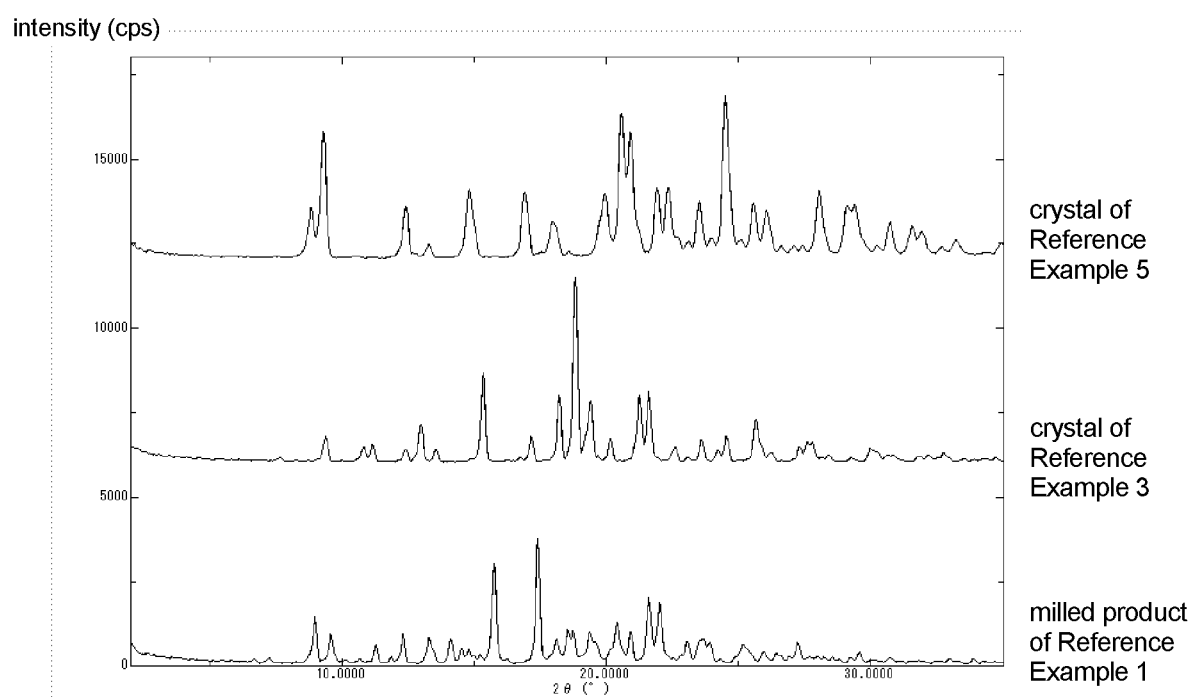
FIG. 4 shows the powder X-ray diffraction patterns of the milled product and crystals obtained in Reference Examples 1, 3 and 5, respectively.

Measurement of Powder X-Ray Diffraction of (4-benzyl-4-hydroxypiperidin-1-yl) (2,4'-bipyridin-3-yl)methanone The powder X-ray diffractions of (4-benzyl-4-hydroxypiperidin-1-yl) (2,4'-bipyridin-3-yl)methanone obtained in Reference Examples 1 and 3 were measured under the following conditions, respectively.
measurement apparatus: RIGAKU Ultima IV
Measurement Conditions
 tube voltage: 40 kV
 tube current: 50 mA
 scan speed: 6°/min
 scan angle (2θ): 2-35°
The 2θ and d value of the powder X-ray diffraction peak of the milled product obtained in Reference Example 1 are shown in Table 1. The obtained powder X-ray diffraction pattern is shown in FIG. 1 and FIG. 4.

TABLE 1

| 2θ(°) | d value(Å) |
|---|---|
| 8.98 | 9.84 |
| 9.58 | 9.22 |
| 11.28 | 7.84 |
| 12.30 | 7.19 |
| 14.10 | 6.28 |
| 15.74 | 5.63 |
| 17.38 | 5.10 |
| 20.90 | 4.25 |
| 21.58 | 4.11 |
| 22.00 | 4.04 |

Figure 2:
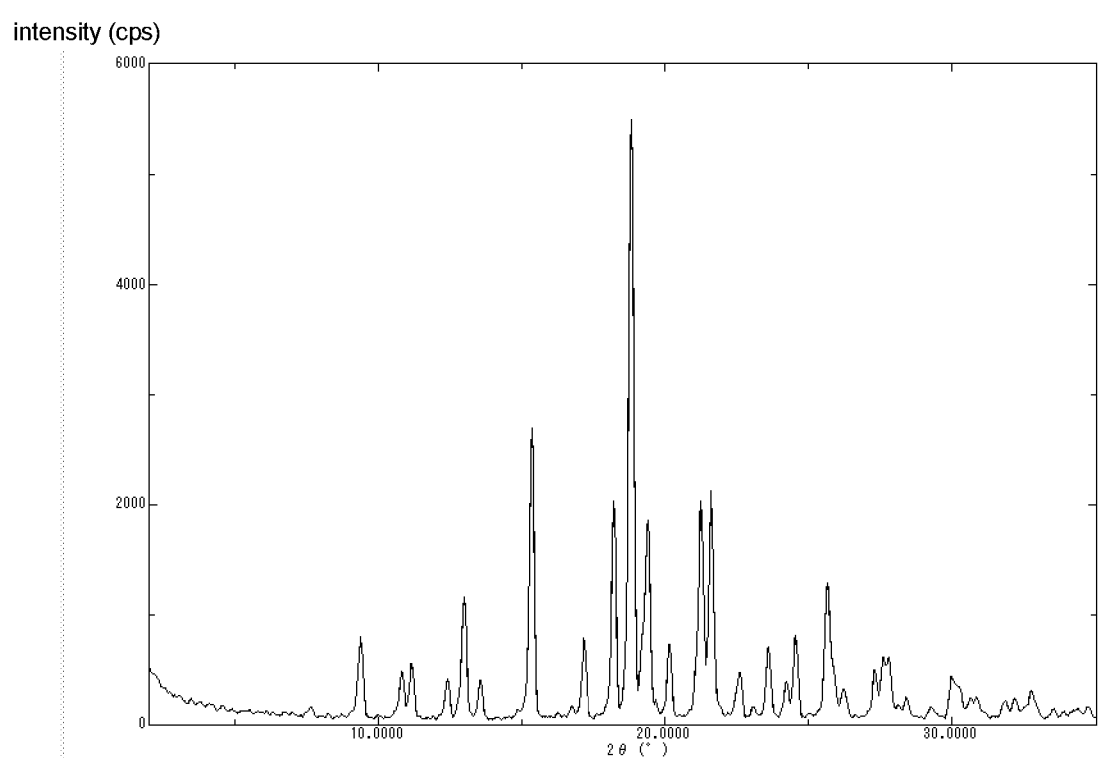
FIG. 2 shows the powder X-ray diffraction pattern of the crystal obtained in Reference Example 3.

The 2θ and d value of the powder X-ray diffraction peak of the crystal obtained in Reference Example 3 are shown in Table 2. The obtained powder X-ray diffraction pattern is shown in FIG. 2 and FIG. 4.

TABLE 2

| 2θ(°) | d value(Å) |
|---|---|
| 9.38 | 9.42 |
| 10.82 | 8.17 |
| 12.98 | 6.81 |
| 15.34 | 5.77 |
| 17.16 | 5.16 |
| 18.20 | 4.87 |
| 18.80 | 4.72 |
| 19.38 | 4.58 |
| 20.14 | 4.41 |
| 21.58 | 4.11 |

Reference Example 5

To (4-benzyl-4-hydroxypiperidin-1-yl) (2,4'-bipyridin-3-yl)methanone (about 9 g) obtained in Reference Example 1 was added 0.5% (w/v) aqueous methyl cellulose solution (about 60 mL), and they were mixed using a conditioning mixer at room temperature for 5 min, and the mixture was refrigerated for 2 day. The crystals were collected by filtration from the suspension after refrigerated.

Figure 3:
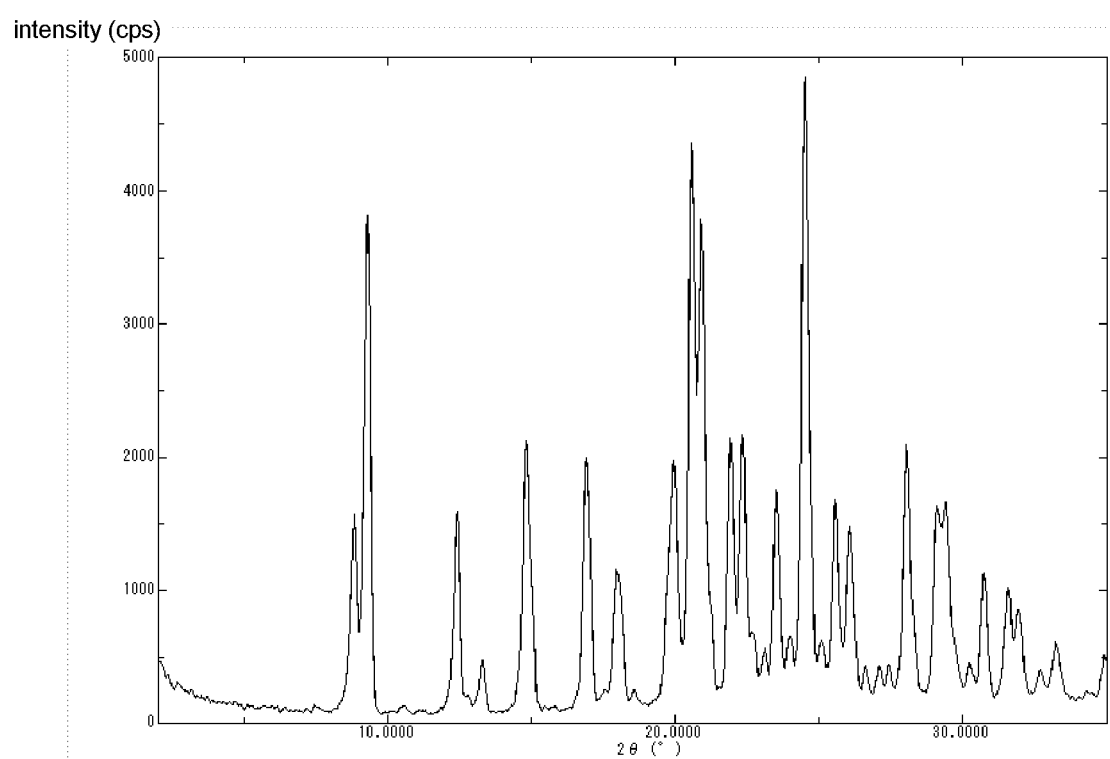
FIG. 3 shows the powder X-ray diffraction pattern of the crystal obtained in Reference Example 5.

The 2θ and d value of the powder X-ray diffraction peak of the obtained crystal, when measured under powder X-ray diffraction measurement conditions described in Reference Example 4, are shown in Table 3. The obtained powder X-ray diffraction pattern is shown in FIG. 3 and FIG. 4.

TABLE 3

| 2θ(°) | d value(Å) |
|---|---|
| 8.84 | 9.99 |
| 9.30 | 9.50 |
| 12.42 | 7.12 |
| 14.78 | 5.99 |
| 16.88 | 5.25 |
| 20.54 | 4.32 |
| 20.90 | 4.25 |
| 21.90 | 4.06 |
| 22.32 | 3.98 |
| 24.48 | 3.63 |

The moisture amount of the obtained crystal was measured under the following conditions. It is clear from the result that the crystal is (4-benzyl-4-hydroxypiperidin-1-yl) (2,4'-bipyridin-3-yl)methanone trihydrate. moisture measurement (Karl Fischer moisture measurement) measurement conditions: room temperature (about 26° C.)/relative humidity about 35%
measurement apparatus: Hiranuma Sangyo Co., Ltd. AQ-7
electrolyte: Aqualyte RS-A
sample amount: about 2 mg

INDUSTRIAL APPLICABILITY

Since the production method of the present invention is suitable for industrial production, it is a very useful method.

This application is based on patent application No. 2015-204164 filed on Oct. 16, 2015 in Japan, the contents of which are encompassed in full herein.

The invention claimed is:

1. A method of producing (4-benzyl-4-hydroxypiperidin-1-yl)(2,4'-bipyridin-3-yl) methanone or a salt thereof, which comprises
    step (1): a step of reacting a 2-halogenonicotinic acid or a reactive derivative thereof or a salt thereof and a 4-benzyl-4-hydroxypiperidine benzoate to give a (4-benzyl-4-hydroxypiperidin-1-yl) (2-halogenopyridin-3-yl)methanone or a salt thereof; and
    step (2): a step of reacting the obtained (4-benzyl-4-hydroxypiperidin-1-yl)(2-halogenopyridin-3-yl) methanone or a salt thereof with pyridine-4-boronic acid or a reactive derivative thereof or a salt thereof in the presence of a metal catalyst and a base to give (4-benzyl-4-hydroxypiperidin-1-yl) (2,4'-bipyridin-3-yl)methanone or a salt thereof.

2. The method of claim 1, wherein the 2-halogenonicotinic acid is 2-chloronicotinic acid.

3. The method of claim 1, wherein the reactive derivative is an acid chloride.

4. The method of claim 1, wherein the metal catalyst is bis(acetylacetonato)palladium(II).

5. The method of claim 1, wherein the base is sodium carbonate.

* * * * *